US00PP27087P3

(12) United States Plant Patent
Dupont, Sr.

(10) Patent No.: US PP27,087 P3
(45) Date of Patent: Aug. 23, 2016

(54) *HIBISCUS* PLANT NAMED 'DUP-CYP'

(50) Latin Name: *Hibiscus rosa-sinensis*
Varietal Denomination: DUP-CYP

(71) Applicant: Dupont Nursery, Inc., Plaquemine, LA (US)

(72) Inventor: Robert J. Dupont, Sr., Plaquemine, LA (US)

( * ) Notice: Subject to any disclaimer, the term of this patent is extended or adjusted under 35 U.S.C. 154(b) by 74 days.

(21) Appl. No.: 14/120,199

(22) Filed: May 5, 2014

(65) Prior Publication Data

US 2015/0319902 P1 Nov. 5, 2015

(51) Int. Cl.
*A01H 5/02* (2006.01)

(52) U.S. Cl.
USPC ..... Plt./257

(58) Field of Classification Search
USPC ..... Plt./257
See application file for complete search history.

*Primary Examiner* — Annette Para
(74) *Attorney, Agent, or Firm* — Cassandra Bright

(57) ABSTRACT

A new and distinct cultivar of *Hibiscus* plant named 'DUP-CYP' characterized by glossy, dark green leaves, very upright habit appropriate for container production and culture, freely flowering habit and a large to very large double flower having a dark red eye zone which is margined against a scarlet body which is margined with bright yellow. The edge of each petal is ruffled, and the petals shallowly overlap.

1 Drawing Sheet

Latin name of the genus and species: *HIBISCUS* PLANT NAMED 'DUP-CYP'.

The present invention relates to a new and distinct cultivar if *Hibiscus*, botanically known as *Hibiscus rosa-sinensis* and hereinafter referred to by the cultivar name 'DUP-CYP'.

*Hibiscus* have been the subject of human admiration for centuries. While the ancestry of present *rosa-sinensis* hybrids is not precisely known, today's hybrids are thought to be the products of interspecific crosses involving Hawaiian, Polynesian and Asian species, among others, some of which may no longer be found in the wild, if at all. It is thought that the first *hibiscus* identified as a '*rosa-sinensis*' was a double red form of uncertain origin found in cultivation in China, India and Polynesia, to be later introduced to Hawaii from Polynesia. It is known to have been grown in Europe during the Victorian era. Eventually, it was introduced to the continental United States where it was cultivated outdoors in the Deep South as well as in regions having subtropical or Mediterranean climates (Florida and Southern California, respectively). Indoor cultivation took place in the temperate regions of the U.S. It is speculated that the original '*rosa-sinensis*' is actually a species hybrid, possibly naturally arising, involving two or more species. Regardless, present day hybrids are descended from the original double form, and are thought to include additional species such as *Hibiscus liliiflorus, H. arnottianus, H. schizopetalus*, and other species, known and unknown, some of which are no longer found in the wild, if at all. Today, after decades of extensive hybridization, the moniker '*rosa-sinensis*' almost certainly denotes complex interspecific hybrids. Such hybrids are usually far removed from their species ancestors in form and color. Flowers of spectacular size, color intensity and, in the last several decades, ringed and spotted patterns have been produced by U.S. hybridizers in Louisiana, Florida, Texas and elsewhere. Other hotbeds of activity include Australia, and more recently, Tahiti. Today's flowers are removed from their species ancestors to such an extent that it is almost impossible to unravel the species component contributions which comprise a modern hybrid *hibiscus*.

However, despite the fact that extensive hybridization was giving rise to larger blossoms and more intense colors, few early hybrids attracted the attention of large scale propagators. While the flowers were some of the most impressive in the entire plant world, hybridizer selection for bloom characteristics alone resulted in weak, short-lived plants. Many varieties were difficult to root from cuttings, and even if they did root, many varieties, when grown on their own roots, were extremely susceptible to fungal and bacterial root rots. Some grew acceptably only as grafted plants. However, grafted plants suffer from a serious disadvantage in that the quality of the graft generally determines the quality of the plant, making the production of uniformly vigorous plants a difficult task. Furthermore, after several years, it is common for grafted plants to develop stresses at the graft union due to the unequal growth rates of the rootstock and the scion. Such stresses can eventually lead to loss of vigor and death of the plant. Moreover, grafting does not completely cure the problem of root rot; surprisingly, the rootstock, when grafted to a root-rot susceptible scion was generally still more likely to suffer rot than a plant of the rootstock variety. For example, a plant of 'Seminole Pink', a garden variety commonly used as a rootstock, is highly resistant to root rot. However, when 'Seminole Pink' is used as a rootstock for 'Romeo', a modern hybrid which is prone to root rot, the grafted plant, while less susceptible than 'Romeo', is more susceptible than a plant of 'Seminole Pink'. Another disadvantage of grafted plants is the introduction of viruses into the scion from the rootstock. Rootstock varieties are almost invariably old garden varieties which, over the years, have become infected with multiple viruses. While the performance of such vigorous garden varieties may be largely unaffected by the virus infection, the hybrid scion of grafted plants were usually significantly less vigorous than the garden variety rootstock, and virus infection from the rootstock resulted in a weak plant. The problem only increased with successive generations of grafting, resulting in a general weakening of a given variety over time.

As a result, the flower production of many modern hybrids was generally sparse with a high number of deformed blooms. Furthermore, buds often took relatively long times to reach blooming stage, and it was not uncommon to wait with anticipation while a bud swelled day by day, only to be disappointed when the mature bud toppled from its pedicel on the day it was to open. Moreover because of hybridizer emphasis on the flower, the plant was often relatively slow growing and sparsely clothed in leaves.

Such characteristics left *hibiscus* with the reputation that, despite the mesmerizing beauty of the flowers, they were for collectors who had time to attend to the seemingly exacting requirements of the plants. As a result, while new varieties were produced by hobbyists yearly, commercial scale propagation of modern hybrids was generally rare. Common garden varieties ('Seminole Pink', 'Brilliant', 'President', 'Painted Lady', 'Butterfly', 'Lagos' and others), which are easy to root, fast growing, and tolerant of a wide range of growing conditions were the only *hibiscus* widely available. The "exotics" have generally been commercially impractical, and thus, of little interest to commercial growers.

Many new varieties of *hibiscus* which represent a vast improvement in *rosa-sinensis* hybrids, have been produced by an intense hybridizing program conducted by the Inventor at his commercial nursery in Plaquemine, La. The objective of the program has been to produce varieties of *hibiscus* which root easily under commercial rooting conditions, grow well on their own roots, maturing rapidly into well-leaved, commercially salable plants under commercial greenhouse conditions. Further objectives are to produce *Hibiscus* cultivars as aforementioned, having large-flowers with unique and desirable flower characteristics, such as size, color intensity and pattern. 'DUP-CYP' was produced by crossing the cultivar 'Magic Moments' (pollen parent) with the cultivar 'Pink Blush' (seed parent). The instant plant was found among the progeny of the stated cross. The instant plant differs from its parents and other hybrid *hibiscus* primarily in flower color. The instant plant generally differs from other hybrid *hibiscus* cultivars in that it roots at a higher percentage of cuttings under commercial rooting conditions, and it grows well on its own roots.

Asexual reproduction of the new *Hibiscus* by hard wood, semi hardwood, and terminal cuttings used in a controlled environment in Plaquemine, La., has shown that the unique features of this new *Hibiscus* are stable and reproduced true to type in successive generations.

The new variety is similar to the seed parent in most horticultural characteristics, however, DUP-CYP differs in the following:

1. The flower of the new variety is double, flower of the seed parent is single.
2. The flower color of the new variety is Yellow, Orange and Red, flower color of the seed parent is pink.

The new variety is similar to the pollen parent in most horticultural characteristics, however, DUP-CYP differs in the following:

1. Flower color of the new variety is Orange, Yellow and Red, flower color of the pollen parent is orange.

The new many known *Hibiscus* cultivars, the new variety can be compared to the unpatented 'Peggy Hendri'. The new variety is similar to this comparator in most horticultural characteristics, including a fully double flower, however, DUP-CYP differs in the following:

1. The flower color of the new variety is Yellow, Orange and Red whereas flower color of this comparator is dark Yellow.
2. Flower diameter of the new variety is larger.
3. Rooting of the new variety is easier than that of this comparator.

The new many known *Hibiscus* cultivars, the new variety can be compared to the unpatented Flame Ball. The new variety is similar to this comparator in most horticultural characteristics, including double flowering. However, DUP-IPD differs in the following:

1. The flower color of the new variety is Yellow, Orange and Red whereas flower color of this comparator is Orange with Yellow blotches.
2. Flower diameter of the new variety is larger.
3. Rooting of the new variety is easier than that of this comparator.

SUMMARY OF THE INVENTION

The cultivar 'DUP-CYP' has not been observed under all possible environmental variables. The phenotype may vary somewhat with variations in environment such as temperature, light intensity, nutrition and water status without, however, any variation in genotype. For example, during cooler weather, flowers may demonstrate an increased intensity in pink tones, particularly in the lighter colored edge zone. Furthermore, as with many varieties of *Hibiscus*, cooler weather can result in a decrease in flower diameter, and a corresponding reduction in size of sepals and pistil. Moreover, as indicated below, plant characteristics vary greatly with culture, with internode spacings often increasing in warmer weather and with higher fixed nitrogen soil content. Plants grown at higher temperatures also exhibit a faster rate of growth. In general the plant used in the following description was grown at temperatures which never dipped below 55° F. Because the Inventor's one gallon plants are grown for an average time of about 5.5 to 6 months prior to sale, and the 10 inch pot plants are grown for an average time of about 7 to 8 months prior to sale, it is difficult to provide a precise temperature profile required to give the average plant measurements described in the below description. The growing period can encompass several seasons, with seasonal fluctuations in high/low temperatures as well as photo period. It is expected that the daily high temperature ranged from about 70° F. to about 95° F., and the daily low temperature, which never dipped below 55° F., ranged from about 65° F. to about 80° F.

The following traits have been repeatedly observed and are determined to be the unique characteristics of 'DUP-CYP'. These characteristics in combination distinguish 'DUP-CYP' as a new and distinct cultivar.

1. Glossy, dark green leaves.
2. Sturdy, very upright habit appropriate for container production and culture.
3. Freely flowering habit.
4. A large double flower having a dark red eye zone which is margined against a scarlet body which is margined with bright yellow.
5. The plant is at least as free-flowering as each parent.

BRIEF DESCRIPTION OF THE PHOTOGRAPH(S)

The accompanying colored photographs illustrate the overall appearance of the new *Hibiscus*, showing the colors as true as it is reasonably possible to obtain in colored reproductions of this type. Colors in the photographs may differ slightly from the color values cited in the detailed botanical description which accurately describe the colors of the new *Hibiscus*.

The photograph on the first sheet is of the front of the bloom.

DETAILED BOTANICAL DESCRIPTION

In the following description, color references are made to The Royal Horticultural Society Colour Chart except where general terms of ordinary dictionary significance are used. The following observations, measurements, and values describe plants grown in Plaquemine, La., with one plant per 1 gallon container. Plants used for the description were plants in standard 1 gallon pot and were about 27 weeks old.

Botanical classification: *Hibiscus rosa-sinensis.*

Parentage:

*Female or seed parent.*—Pink Blush (not patented).

*Male or pollen parent.*—Magic Moments (not patented).

Propagation:

*Type.*—Cuttings 'DUP-CYP' has been propagated by taking hardwood, semi hardwood, and tip cuttings, with semi hardwood preferred. It should be noted that many methods of asexual propagation, such as tissue culture and other cloning processes, can be expected to show some degree of success in the propagation of the present cultivar, although. However, of the methods tried by the inventor, the use of semi hardwood cutting has given the greatest yield of commercially salable plants. Asexual propagation has resulted in plants which have the flower and plant characteristics of the original 'DUP-CYP' plant, and thus the variety is stable.

Cuttings from 'DUP-CYP' generally root well under commercial greenhouse conditions. While greenhouse conditions such as relative humidity and other factors such as cutting age prior to planting affect the take, it is not unusual to get a take of almost 100%. Please note that as successive generations of cuttings are raised, the raiser may experience a drop in take due to the incorporation of virus, particularly if at some point grafted plants are prepared, and cuttings are taken from such a plant.

*Time to initiate roots.*—An average time of initiation at approximately 22° C. is approximately six weeks, with slightly longer times during winter at comparable temperatures, and slightly shorter during summer at comparable temperatures.

*Time to develop roots.*—An average time, at approximately 22° C., of development of a root system after initiation, is approximately six weeks, with slightly longer times during winter at comparable temperatures, and slightly shorter during summer at comparable temperatures. It should be noted that root initiation and development can be affected by greenhouse conditions, biological stressors such as disease organisms, as well as environmental stressors such as low or variant relative humidity, over-and under-watering, temperature variations or high or low constant temperatures. Thus, rooting times can be shorter or longer than the times given above depending on the values of many different characteristics during the rooting process known in the art.

*Root description.*—Fibrous and well-branched.

Plant description:

*Plant form and growth habits.*—Perennial evergreen having Very upright, rangy growth. Generally somewhat compact, but internodal space can be dependent upon greenhouse temperature time profile, fertilizer level, and other factors.

*Branching habit.*—Sparsely-branched, having approximately 4-5 laterals when a single stem plant is pinched back to a 5 inch height.

*Plant height, soil level to top of flowers.*—A salable plant in a 1 gallon pot can be approximately 18 inches high and 7 inches wide. Please note that cultural variables such as greenhouse temperature time profile, fertilizer time profile, and other factors can cause significant variation from the above values.

*Lateral branch description.*—The average branch characteristics of a salable 1 gallon plant: Average Length: approximately 10". Average Diameter: approximately 0.6 cm measured at the transition from green to woody stem texture. Texture: Immature, smooth; mature, woody and rough. Color: Immature: Green, more green than 147A. Mature: Brownish gray, close to 200C with 197A overtones.

Mature foliage description:

*Arrangement.*—Alternate, single; numerous; symmetrical.

*Length.*—Approximately 11.1 cm.

*Width.*—Approximately 9.6 cm.

*Shape.*—Rounded to cordate. Apex: acute.

*Margin.*—Crenate. Texture: upper surface: glabrous, rugose; lower surface: glabrous, rugose.

*Color.*—Young foliage, upper surface: More green than 147A; very glossy. Mature foliage, upper surface: Generally darker than 147A; glossy. Typical color of undersurface of mature leaf: 147A. Typical color of undersurface of immature leaf: more yellow than 147A.

*Shape of typical foliage base.*—Rounded to cordate.

*Petiole.*—Average Length: 3.0 cm. Average Diameter: 0.3 cm. Texture: Fine pubescence on upper surface; lower surface, glabrous. Typical petiole color: 147A. Color: Dark greenish brown; close to 200A with undertones of 147A. It should be noted that as with other plant growth characteristics foliage color and size can vary somewhat with fertilization regimen, greenhouse temperature, day length, and other conditions of culture.

Flower description:

*Natural flowering season.*—Year round, with number and size reduction in extended periods of cold weather, such as daytime temperatures of less than 60° C. Extreme heat can slow growth and flower production.

*Flower arrangement.*—Flowers arranged singly at terminal leaf axils. Very free-flowering, with usually about two to three developing flower buds per lateral branch, flowers face mostly upright.

*Flower appearance.*—Large, double flowers. Flowers are open for one to two days before senescence, which is often accompanied by partial or full petal closure. Flowers persistent.

*Flower diameter.*—'DUP-CYP' flowers are generally in the range of from about 6.5" to 8.5" when fully open, with largest flowers produced during warm weather (for example, day and night time temperatures above 73° F.

*Flower depth*.—Flower depth was measured to average approximately 4.5 cm. Flower depth was measured after removal of a petal and a sepal to expose the base of the pistil. The measurement was taken on a fully opened flower in the direction of the pistil, from the base of the ovaries to the maximum height of the flower petal, which is the point of recurvature of the petal. It should be noted that *hibiscus* blossoms can flatten out during the day, or increase or decrease in curvature or degree of petal reflex during the day, and thus variance from the foregoing value is possible.

*Flower bud* (*just before showing color*).—

Rate of opening: 1-2 days. Rate of opening is generally faster in warmer weather. Flower bud dimensions were measured on a bud which was approximately one day from opening. The measurements were as follows. Bud length was measured from the abscission zone where bud and peduncle meet to the tip of the bud. The average length of a bud which is one day from opening is approximately 6.0 cm. Bud diameter was measured at the widest part of the bud, an area approximately halfway up the outside of the developing petals. The average diameter of a bud which is one day from opening is approximately 1.6 cm. It should be noted that bud dimensions can vary somewhat with cultural conditions, and variations can even be observed in buds which are at the same stage of development.

*Shape*.—Acuminate. Typical color of unopened bud: More green than 147A.

*Petals*.—Texture: Smooth, satiny, rugose. Arrangement: The corolla consists of five base petals arranged in a whorl, having regular partial overlap. The flower is a lose double having very few flower parts, with a high degree of petaloid tissue. Shape: roughly spatulate, with a rounded apex and a truncate base. The margin of each petal heavily undulate and entire, such that the margin of the flower appears to be broadly undulate, and the overlap is such that the flower margin appears almost circular, with indentations at the point where the flower margin changes from one petal to the adjacent petal. A representative length was measured to be 9 cm, and was taken from the base of the petal to the farthest point on the margin opposite the base. A representative width is 7 cm, and was measured perpendicularly to the pistil at the widest point of the petal. Petal size can vary with cultural conditions, such as temperature, and thus the flower size and shape can vary as well. Often, flowers which are produced at colder temperatures are smaller and appear more fully overlapped, giving almost a wheel-shaped appearance. The color of a warm weather flower is described below. It has been observed that colder temperatures can result in the stronger expression of pink tones, especially in pink regions of each petal. It should be noted that the colors of *hibiscus* are among the most changeable of all flowers. A newly opening morning bloom generally has the most intense coloration, but as the flower flattens out and is exposed to the sun, many pigments begin to fade immediately, resulting in a flower which can look like a different variety altogether. The flower of 'DUP-CYP' can fade to a dull red body and straw colored edge. The morning colors are described below.

*Color*.—Upper surface: Margin: Near R.H.S. Yellow-Orange 15C. Center: Near R.H.S. Orange 24B; veins: Near R.H.S. Red 42A. Base: Near R.H.S. Red 46A. Lower surface: Overlapping side: Near R.H.S. Orange 24B. Underlapping side: Near R.H.S. Yellow-Orange 23B. Venation: Near R.H.S. Red 42A.

*Sepals*.—Unlike the petals, sepals are relatively invariant in color. Their size can be affected by same cultural conditions which affect flower size, They are generally smooth and elongated oblong with acute apices (pointed tips). They are fused at the long edges into a cupped calyx bearing at its brim the five pointed tips. When the petals of the flower spread open, the five pointed tips, which are flush with the backs of the opening petals, are forced into a radiating five point star-shaped configuration, which can be observed on the profile and reverse pictures. A representative width, which is measured perpendicularly to the long axis of the sepal a at the position on the sepal at which the oblong edges transition from fused to unfused, is approximately 1.5 cm. A representative length, measured on the sepal from the free point to the fused point is approximately 2.5 cm. Color: Upper surface: Close to R.H.S. Green 137A. Lower surface: Close to R.H.S. Green 137A. Both upper and lower sepal surfaces glabrous.

*Epicalyx*.—5-7, most commonly 6 sepals; more green than 147A. Both surfaces glabrous. Length of [2] cm on a fully opened bloom.

*Peduncle*.—Length: 5 cm. Angle: approximately 45 degrees from vertical. Strength: Strong, flexible. Texture: smooth. Typical peduncle diameter: 0.9 to 1.2 cm. Typical peduncle color: Slightly darker than 146A.

Reproductive organs:

*Androecium*.—Stamen number: approximately 10-30. Anther shape: crescent. Anther color: Near R.H.S. Yellow-Orange 15A. Amount of pollen: moderate. Pollen color: Near R.H.S. Yellow-Orange 15B. Typical filament length: approximately 1.5 cm. Typical filament color: Near R.H.S. Yellow 12B. Typical anther length, including filament, upon dehiscence: 2 mm.

*Gynoecium*.—Typical ovary color: 150C. Pistil number: 0-1. Pistil length (from base of ovaries to top of stigma): About 8 cm. Style length (from base of ovaries to stigma branching point):

*About* 7 cm.—Stigma length: about 0.5 cm. Style diameter, at base: 0.4 cm. Style color: Base: Near R.H.S. Yellow 13C. Midsection: Near R.H.S. Yellow 13C. Apex: Near R.H.S. Yellow 13C. Stigma number: 0-3. Stigma color: Near R.H.S. Yellow 13C.

It should be noted that the dimensions of a *hibiscus* blossom generally change not only during bud development, but also during opening, as well as during the life of the opened flower. For instance, upon opening, the petals generally gain in length. Double varieties gain significant mass during opening. Furthermore, after opening, the pistil continues to grow in length while the anther filaments which hold the pollen sacs increase in length, the pollen sacs open and the stigmas separate, each at the tip of a branched style structure. Toward the end of the flower life, possibly due to a reduction in turgor pressure, the pistil may shrink in length and the petals may slightly decrease in area. Usually, the senescing petals of the flower fold toward the pistil to some degree, in some cases, completely enfolding it.

'DUP-CYP' is known to occasionally bloom semi-double or single.

Seeds are not typically produced and are unlikely to be observed under most growing conditions.

*Disease resistance.*—

'DUP-CYP' has not been observed to be resistant to pathogens common in *hibiscus*. However, it has been observed in the green house to have a higher resistance to root rot than that of many existing hybrid varieties grown on their own roots known to the Inventor.

If desired, and if a the risk of virus infection is of no concern, the present variety can be grafted onto a rootstock and be grown as a grafted plant.

It is claimed:

1. A new and distinct *hibiscus* plant named 'DUP-CYP', as illustrated and described.

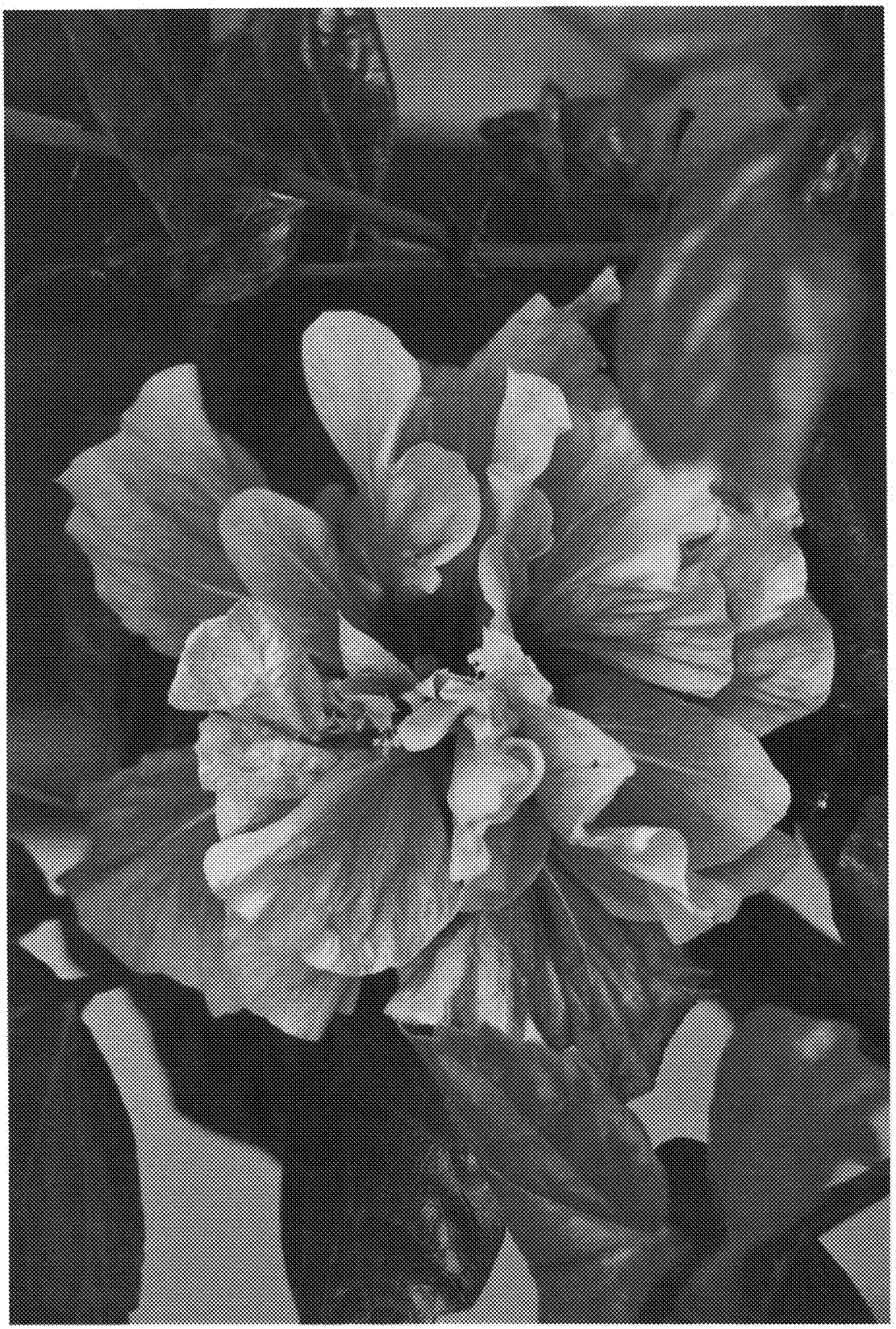

* * * * *